United States Patent [19]

Humber et al.

[11] 4,258,183

[45] Mar. 24, 1981

[54] PROCESS FOR THE PREPARATION OF CEPHALOSPORIN COMPOUNDS

[75] Inventors: David C. Humber, London; Stuart B. Laing, Harrow; Gordon G. Weingarten, London, all of England

[73] Assignee: Glaxo Group Limited, London, England

[21] Appl. No.: 77,758

[22] Filed: Sep. 20, 1979

Related U.S. Application Data

[63] Continuation-in-part of Ser. No. 27,804, Apr. 6, 1979, abandoned.

[30] Foreign Application Priority Data

Apr. 6, 1979 [GB] United Kingdom ............ 12215/79

[51] Int. Cl.³ .......................................... C07D 501/02
[52] U.S. Cl. ........................................ 544/22; 544/21
[58] Field of Search .................................. 544/21, 22

[56] References Cited

U.S. PATENT DOCUMENTS

| | | | |
|---|---|---|---|
| 3,355,452 | 11/1967 | Urech et al. | 544/16 |
| 3,875,152 | 4/1975 | Sellstedt | 544/28 |
| 3,905,967 | 9/1975 | Webber | 544/22 |
| 4,043,991 | 8/1977 | Hamma et al. | 544/21 |

OTHER PUBLICATIONS

Shokol et al., Chemical Abstracts, vol. 73, 14927b (1970).
Cotton et al., Advanced Inorganic Chemistry, (1967) pp. 506–508.

*Primary Examiner*—Paul M. Coughlan, Jr.
*Attorney, Agent, or Firm*—Bacon & Thomas

[57] ABSTRACT

A process for the preparation of a 3-carbamoyloxymethyl cephalosporin compound which comprises hydrolyzing a 3-phosphonocarbamoyloxymethyl cephalosporin compound. The hydrolysis is preferably effected at a pH in the range of pH3 to 4, for example using aqueous sodium hydrogen carbonate.

3 Claims, No Drawings

PROCESS FOR THE PREPARATION OF CEPHALOSPORIN COMPOUNDS

This Application is a continuation-in-part of our pending Application Ser. No. 27804 filed Apr. 6, 1979 abandoned.

This invention is concerned with the preparation of cephalosporin compounds substituted at the 3-position by a carbamoyloxymethyl group.

The cephalosporin compounds in this specification are systematically named with reference to "cepham" after *J. Amer. Chem. Soc.*, 1962, 84, 3400; the term "cephem" refers to the basic cepham structure with one double bond.

Many cephalosporin compounds possessing a degree of antibacterial activity are known in the art. These compounds possess $\Delta^3$ unsaturation and are ordinarily substituted at the 3-position by a methyl or substituted methyl group, at the 4-position by a carboxy group, and at the 7$\beta$-position by an acylamido group. In some instances the compounds may additionally be substituted at other positions, for example at the 2-position (e.g. by one or two methyl groups or a methylene group) and/or at the 7$\alpha$-position (e.g. by a lower alkyl, alkoxy or alkylthio group).

One class of cephalosporin antibiotics which has attracted considerable interest comprises compounds substituted at the 3-position by a carbamoyloxymethyl group, i.e. the group $-CH_2.O.CO.NH_2$; a number of antibiotics of this type, possessing a variety of 7$\beta$-acylamido groups, have been proposed.

These 3-carbamoyloxymethyl cephalosporin compounds may usefully be prepared by reacting a 3-hydroxymethyl cephalosporin compound with a substituted isocyanate, i.e. a compound of formula

R.NCO  (I)

where R is a labile protecting group, e.g. a trichloroacetyl, 2,2,2-trichloroethoxycarbonyl or chlorosulphonyl group. This reaction leads to formation of an N-mono-substituted 3-carbamoyloxymethyl cephalosporin wherein the 3-position substituent has the formula

—CH$_2$.O.CO.NHR where R is as defined above; the labile group R may be cleaved from this product by, for example, hydrolytic, reductive or acid-induced cleavage as appropriate, to yield the desired 3-carbamoyloxymethyl cephalosporin.

A disadvantage of previously proposed processes of the above type is that the isocyanates of formula (I) which have hitherto been suggested as appropriate carbamoylating agents tend to be somewhat difficult or inconvenient to prepare, for example involving hazardous and/or expensive reagents. Moreover these reagents and the resulting isocyanates may be difficult or impossible to transport. Thus, for example, the preparation of carbamoylating agents such as chlorosulphonyl isocyanate and trichloroacetyl isocyanate typically involve reaction of sulphur trioxide with cyanogen chloride and trichloroacetamide with oxalyl chloride respectively.

We have now discovered that 3-carbamoyloxymethyl cephalosporins may be prepared in high yield by hydrolysis of 3-phosphonocarbamoyloxymethyl (3-CH$_2$O.CO.NH.PO(OH)$_2$) cephalosporins. Such phosphonocarbamoyloxymethyl cephalosporins may be  pared in relatively simple and economic manner, if desired without isolation.

Thus according to one aspect of the present invention there is provided a process for the preparation of a 3-carbamoyloxymethyl cephalosporin compound which comprises hydrolysing a 3-phosphonocarbamoyloxymethyl cephalosporin compound.

In a preferred embodiment of the process of the present invention, there is provided a process for the preparation of compounds of general formula

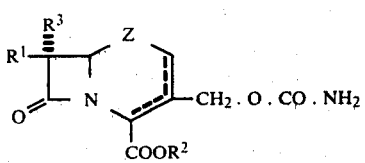

[wherein $R^1$ represents a protected amino group (e.g. an acylamido group, conveniently one which contains 1–40, e.g. 1–20, carbon atoms, or a precursor therefor); $R^2$ represents hydrogen or a carboxyl blocking group (e.g. the ester-forming residue of an alcohol, phenol, silanol or stannanol, the residue preferably being one which may readily be split off at a later stage); $R^3$ represents hydrogen or a lower (e.g. $C_{1-4}$) alkyl, alkylthio or alkoxy group e.g. a methoxy group; Z is $>S$ or $>S\rightarrow O$ ($\alpha$- or $\beta$-); and the dotted line bridging the 2-, 3- and 4-positions of the molecule indicates that the compounds may be ceph-2-em or ceph-3-em compounds] and, where appropriate, salts thereof, which comprises hydrolysing a compound of formula

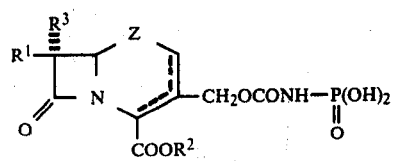

(wherein $R^1$, $R^2$, $R^3$, Z and the dotted line are as hereinbefore defined) and salts thereof, whereafter if necessary and/or desired any of the following reactions in any appropriate sequence may be carried out:

(i) conversion of a precursor for a desired acylamido into that said group, e.g. by removal of a protecting group, (ii) conversion of a $\Delta^2$ isomer into a desired $\Delta^3$ isomer, (iii) removal of any carboxyl blocking group or any hydroxyl or amino protecting groups, and (iv) reduction of a cephalosporin sulphoxide product to yield the corresponding sulphide; and finally recovering the desired compound of formula II, if necessary and/or desired after separation of any isomers and/or after conversion of the compound to a salt thereof.

It should be noted that the cephalosporin formulae herein are skeletal formulae and are intended to embrace closely related analogues such as 2-methyl, 2-methylene and 2,2-dimethyl cephalosporins.

Preferred compounds of formula II which may be prepared by the process of the invention are compounds of formula

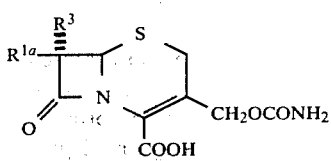

(wherein R$^{1a}$ represents an acylamido group, conveniently one which contains 1 to 40 e.g. 1 to 25 carbon atoms; and R$^3$ is as defined above) and non-toxic derivatives thereof.

The term "non-toxic" as applied to the derivatives of the compounds of formula II' means those derivatives which are physiologically acceptable in the dosages at which they are administered. Such derivatives may include, for example, salts, physiologically acceptable esters, 1-oxides and solvates, e.g. hydrates, of the compounds of formula II' and, where appropriate, combinations thereof.

The compounds of formula II' and non-toxic derivatives thereof which may be prepared by the process of the invention are characterised by antibacterial activity against a range of gram-positive and gram-negative organisms coupled with stability in the presence of serum.

The above compounds of formulae II, II' and III may be capable of forming base salts such as alkali metal, e.g. sodium or potassium, alkaline earth metal, e.g. calcium, ammonium and organic amine, e.g. procaine, 1-aminodamantane, phenylethylbenzylamine, dibenzylethylene diamine, ethanolamine, diethanolamine, triethanolamine, N-methylglucosamine and amino acid (e.g. lysine, arginine, ornithine and histidine in the d-, l- and dl-forms) salts.

A particularly preferred product of the process of the invention is (6R,7R)-3-carbamoyloxymethyl-7-[Z-2-(fur-2-yl)-2-methoxyiminoacetamido]ceph-3-em-4-carboxylic acid, having the approved name of cefuroxime and non-toxic derivatives thereof, which may be prepared by hydrolysis of the corresponding compound (6R,7R)-3-phosphonocarbamoyloxymethyl-7-[Z-2-(fur-2-yl)-2-methoxyiminoacetamido]ceph-3-em-4-carboxylic acid or a salt thereof.

The hydrolysis of the 3-phosphonocarbamoyloxymethyl cephalosporin is conveniently carried out in aqueous solution. The reaction medium may thus be water alone or in combination with a suitable water miscible inert organic solvent. Solvents which may be used include ethers such as tetrahydrofuran and dioxan.

The hydrolysis reaction of the process of the invention is generally effected at a pH below 5 and preferably at a pH in the range pH3 to 4. In order to work in this range it may be appropriate to add either acid or base to the reaction mixture. In the hydrolysis, it may be desirable to buffer the aqueous system, e.g. with sodium carbonate, sodium hydrogen carbonate, sodium acetate, sodium phospate, calcium carbonate or calcium hydroxide, or add an acid or base, e.g. sodium hydroxide, during the course of the hydrolysis in order to maintain the pH within any desired limits. The use of aqueous sodium hydrogen carbonate has proved to be particularly convenient in the hydrolysis reaction.

The hydrolysis may, for example, be conducted at a temperature in the range of −5° to +105° C., e.g. +15° to +60° C., and may, where necessary, be monitored by, for example, chromatography. The reaction time may be significantly affected by both the temperature and pH of the reaction system.

After completion of the hydrolysis the desired 3-carbamoyloxymethyl cephalosporin of formula II may be isolated by, for example, conventional methods, e.g. by solvent extraction where the product is a carboxyl protected derivative such as an ester, or by acidification and precipitation or by extraction where the cephalosporin compound is a free acid or a salt.

The starting materials of formula III for use in the process of the invention may conveniently be prepared from a corresponding 3-hydroxymethyl cephalosporin of formula

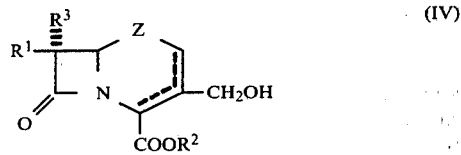

(wherein R$^1$, R$^2$ and R$^3$, Z and the dotted line are as hereinbefore defined), for example, by reaction with dihalophosphinyl isocyanates of formula X$_2$.PO.NCO (wherein each X represents a halogen atom, such as chlorine) followed by reaction with water, conveniently at a pH of 10 or less. The dihalophosphinyl isocyanates may be prepared in relatively simple and economic manner e.g. by reaction of an appropriate phosphorus pentahalide with a carbamic acid ester. If desired, the starting material of formula III for use in the process of the present invention may be prepared in situ and subsequently hydrolysed without isolation to give the desired 3-carbamoyloxymethyl cephalosporin product. However, if it is desired to isolate a compound of formula III, the initial reaction with water is desirably effected at a pH of from 5 to 10.

Acylamido groups which may be present at the 7-position of cephalosporin starting materials and products in the process of the invention e.g. as the group R$^1$ in formulae (II) to (IV) may, for example, be selected from the wide range of side chain acylamido groups known in the β-lactam antibiotic art. It will be appreciated that where the acylamido group carries substituents such as amino, hydroxy or mercapto groups, these substituents may, if necessary and/or desired, be protected by substitution with an appropriate group. Thus, for example, amino groups may be protected by substitution with a mono- or di-valent blocking group, suitable groups including acyl groups, for example lower alkanoyl such as acetyl, substituted lower alkanoyl, e.g. lower haloalkanoyl or phenylacetyl and aroyl such as benzoyl or phthaloyl; lower alkoxycarbonyl or t- butoxycarbonyl and substituted lower alkoxycarbonyl groups e.g. lower haloalkoxycarbonyl such as 2,2,2-trichloroethoxycarbonyl; aryl-lower alkoxycarbonyl groups such as benzyloxycarbonyl; sulphonyl groups, for example lower alkylsulphonyl such as methanesulphonyl and aryl-sulphonyl such as benzene sulphonyl or p-toluene sulphonyl; ylidine groups formed by reaction with an aldehyde or ketone which forms a Schiff's base, for example acetone, methylethylketone, benzaldehyde, salicylaldehyde or ethyl acetoacetate; and divalent groups such that the nitrogen atoms forms part of a dihydropyridine ring (protecting groups of this last sort being obtained by, for example, reaction with formaldehyde and a β-ketoester, e.g. acetoacetic ester, as described in Belgian Pat. No. 771,694). Hydroxyl and mercapto groups may for example, be protected by substitution with carboxylic or sulphonic acyl groups in like manner to amino groups, or, where appropriate, by etherification or thioetherification (e.g. to introduce a branched lower alkyl group such as isopropyl or t-butyl or an aralkyl group such as benzyl, benzyl substituted by one or more methoxy groups, diphenylmethyl or triphenylmethyl). The protecting groups may subsequently be removed from the cephalosporin product by methods well known in the art, for example by hydrolytic, reductive or acid-induced cleavage as appropriate.

Where the acylamido group is substituted by a carboxyl group it may also be advantageous to protect this during the course of the reaction, for example by etherification to introduce an ester group as herein described in connection with the group $R^2$.

Specific acyl groups which may be present in acylamido groups $R^1$ are illustrated in the following list, which is not intended to be exhaustive:

(i) $R^uC_nH_{2n}CO-$ where $R^u$ is aryl (carbocyclic or hetercyclic), cycloalkyl, substituted aryl, substituted cycloalkyl, cycloalkadienyl, or a non-aromatic or mesionic group, and n is an integer from 1 to 4. Examples of this group include phenylacetyl wherein the phenyl group may if desired be substituted by, for example, one or more of fluoro, nitro, protected amino, protected hydroxy (e.g. esterified hydroxy such as acetoxy), methoxy, methylthio or methyl; N,N-bis(2-chloroethyl-)aminophenylpropionyl; thien-2- and -3-ylacetyl; 3- and 4-isoxazolylacetyl either substituted or unsubstitued; pyridylacetyl; tetrazolylacetyl; cyclohexadienylacetyl; or a sydnonacetyl group. Where n is other than 0, especially where n is 1, the α-carbon atom of the acyl group may be substituted by, for example, an esterified hydroxy (e.g. acyloxy such as formyloxy or lower alkanoyloxy), etherified hydroxy (e.g. methoxy), protected amino (e.g. as hereinbefore described), carboxy, esterified carboxy, triazolyl, tetrazolyl or cyano group or a halogen atom; examples of such α-substituted acyl groups include esterified 2-hydroxy-2-phenylacetyl, N-blocked 2-amino-2-phenylacetyl carboxy-2-phenylacetyl and esterified 2-carboxyacetyl phenylacetyl.

(ii) $C_nH_{2n+1}CO-$ where n is 0 or an integer from 1 to 7. The alkyl group may be straight or branched and, if desired may be interrupted by an oxygen or sulphur atom and/or may be substituted by, for example, a cyano group, a carboxy or esterified carboxy group (e.g. an alkoxy-carbonyl group), an esterified hydroxy group, a blocked amino group or a carboxycarbonyl (—CO.COOH) or esterified carboxycarbonyl group. Examples of such groups include formyl, cyanoacetyl, butylthioacetyl, hexanoyl, heptanoyl, octanoyl, glutaroyl, esterified glutaroyl, and N-blocked (e.g. N-ethoxycarbonyl or N-benzoyl) and optionally esterified R-5-amino-5-carboxypentanoyl (e.g. R-5-benzamido-5-diphenylmethoxycarbonylpentanoyl or R-5-diphenylmethoxycarbonyl-5-isobutoxycarbonylaminopentanoyl).

(iii)

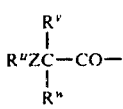

where $R^u$ has the meaning defined under (i) and in addition may be benzyl, $R^v$ and $R^w$ (which may be the same or different) each represents hydrogen, phenyl, benzyl, phenethyl or lower alkyl and Z is an oxygen or sulphur atom. Examples of such groups include phenoxyacetyl, 2-phenoxy-2-phenylacetyl, phenoxypropionyl, 2-phenoxybutyryl, benzyloxycarbonyl, 2-phenoxypropionyl, 2-phenoxybutyryl, methylthiophenoxyacetyl, phenylthioacetyl, chloro- and fluoro- phenylthioacetyl, pyridylthioacetyl and benzylthioacetyl.

(iv) Substituted glyoxylyl groups of the formula $R^y$.-CO.CO-where $R^y$ is an aliphatic, araliphatic or aromatic group, e.g. phenyl, thienyl or furyl or a fused benzene ring. Also included in this class are the α-carbonyl derivatives of the above substituted glyoxylyl groups, e.g. the α-alkoxyimino, α-aryl-oxyimino and α-acyloxyimino derivatives, especially those possessing the syn-configuration with respect to the 7-carboxamido group. Groups of this type, of which an example is the Z-2-(fur-2-yl)-2-methoxyiminoacetyl group, and which may be represented by the formula

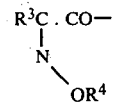

[wherein $R^3$ represents hydrogen or an organic group (especially a carbocyclic or heterocyclic aromatic group such as phenyl, naphthyl, thienyl, thiazolyl e.g. aminothiazolyl, or furyl) and $R^4$ represents hydrogen, an acyl group (e.g. a lower alkanoyl, alkenoyl, alkynoyl, haloalkanoyl, alkoxycarbonyl, haloalkoxycarbonyl, alkylthiocarbonyl or aralkyloxycarbonyl group or an aroyl or carbamoyl group) or an etherifying group (e.g. a lower alkyl, alkenyl, alkynyl, cycloalkyl, cycloalkenyl or aralkyl group or carbocyclic or heterocyclic aryl group, or any of these groups substituted by a carboxy, esterified carboxy, aminocarbonyl or N-substituted aminocarbonyl group)], are described in greater detail in Belgian Pat. Nos. 778630; 783449; 801997; 806450; 823651 and 843152.

Where $R^2$ in formulae (II) to (IV) represents an esterifying group this may, for example, be selected from the wide range of esterifying groups known in the cephalosporin art. A range of groups of this type, together with methods for their introduction and subsequent removal, are described in British Pat. No. 1342241. Representative esterifying groups thus include aryl lower alkyl groups such as p-methoxybenzyl, p-nitrobenzyl and diphenylmethyl; lower alkyl groups such as t-butyl; and lower haloalkyl groups such as 2,2,2-trichloroethyl. It will of course be appreciated that $R^2$ may represent an ester group in a compound which is to be used in medicine in which case this group should be physiologically acceptable. When such an ester group is employed it may not be necessary or desirable to effect deprotection of the carboxyl group.

Where at the end of a given preparative sequence the sulphoxide analogue of the compound of formula (II) is obtained, conversion to the corresponding sulphide may, for example, be effected by reduction of the corresponding acyloxysulphonium or alkyloxysulphonium salt prepared in situ by a known method, such as is described in British patent specification No. 1453049.

As also described in British patent specification No. 1453049 a ceph-2-em-4-carboxylic ester may be coverted into a desired ceph-3-em compound by treatment of the former with a base.

The following Examples illustrate the present invention.

NOTES ON EXPERIMENTAL

All temperatures are quoted in °C. Structures of the products of Examples 2 and 3 were confirmed by infrared and nuclear magnetic resonance spectra, the latter being effected at 100 MHz.

T.l.c. is thin-layer chromatography using pre-coated plates (Merck $F_{254}$, 0.25 mm thick coating) which were examined under ultraviolet light at 254 nm and were developed by spraying with ninhydrin in n-butanol and heating to approx. 140° C. or by exposure to iodine vapour.

PREPARATION 1

(6R,7R)-3-Phosphonocarbamoyloxymethyl-7-[Z-2-(fur-2-yl)-2-methoxyiminoacetamido]ceph-3-em-4-carboxylic acid Dichlorophosphinyl isocyanate (5.28 g) in dioxan (20 ml) was added to a stirred suspension of (6R,7R)-3-hydroxymethyl-7-[Z-2-(fur-2-yl)-2-methoxyiminoacetamido]-ceph-3-em-4-carboxylic acid (11.44 g) in dioxan (80 ml) at 16° in a water bath; after initial addition of the isocyanate the temperature rose to 24° and eventually fell to 17°. After 10 minutes the solution was filtered under nitrogen and 1 molar aqueous sodium bicarbonate solution (192 ml) was added to give a pH of 7.1. The solution was extracted with ethyl acetate (2×150 ml) to remove lactone impurity. Ethyl acetate (150 ml) was then added to the aqueous phase (pH 8.2) and the pH was adjusted to 0.5 by addition of concentrated hydrochloric acid. The resultant two phase suspension was separated and the aqueous suspension extracted with n-butanol (3×250 ml). Water (30 ml) was added to the butanol extract and the aqueous layer was run off. The organic phase was evaporated in vacuo to a thick slurry. Filtration of this slurry afforded a solid which was washed with ether (3×50 ml) and dried in vacuo for 20 hours to give the title compound solvated with ca 1 mole of n-butanol (5.54 g), $[\alpha]_D^{20}+45°$ (c 0.93, pH 7 phosphate buffer); $\lambda_{max}$ 273 nm ($E_{1\ cm}^{1\%}$ 298).

The aqueous suspension was filtered to give a solid which was washed with n-butanol (30 ml) and ether (100 ml) and dried in vacuo to give the title compound (4.37 g), $[\alpha]_D^{21}+44°$ (c 0.96, pH 7 phosphate buffer); $\lambda_{max}$ 273 nm ($E_{1\ cm}^{1\%}$ 317).

PREPARATION 2

(6R,7R)-3-Phosphonocarbamoyloxymethyl-7-[Z-2-(fur-2-yl)-2-methoxyiminoacetamido]ceph-3-em-4-carboxylic acid trisodium salt Portions (5.04 g and 5.73 g) of the first product obtained in Preparation 1 were dissolved in solutions of sodium bicarbonate (2.52 g and 2.86 g) in water (35 ml). The solutions (pH 6.7) were applied to columns containing Amberlite XAD-2 resin [1 kg. previously washed with methanol (5 liters) and water (20 liters)]. The columns were eluted with water and fractions (ca 50 ml) were collected and examined by TLC. Fractions 15 to 25 for each product were combined (pH 8.3 and 7.5) and freeze-dried to give a solid material (3.15 g and 2.80 g).

The two solids were combined, dissolved in water (50 ml) and re-chromatographed on the same column [after washing through with water (2 liters)]. Fractions (ca 50 ml) were collected and examined by TLC. Fractions 22 to 30 were combined and freeze-dried to give the *title compound* (1.02 g), $[\alpha]_D^{21}+41.8°$ (c 1.037, $H_2O$); $\lambda_{max}$ 275 nm ($E_{1\ cm}^{1\%}$ 297).

PREPARATION 3

(a) (6R,7R)-3-Dimethoxyphosphorylcarbamoyloxymethyl-7-[Z-2-(fur-2-yl)-2-methoxyiminoacetamido]ceph-3-em-4-carboxylic acid A solution of dimethoxyphosphinyl isocyanate (7.25 g), in dry tetrahydrofuran (4 ml) was added to a solution of (6R,7R)-7-[Z-2-(fur-2-yl)-2-methoxyiminoacetamido]-3-hydroxymethylceph-3-em-4-carboxylic acid (6.10 g) in dry THF (40 ml) and the resultant mixture was stirred at room temperature for 1.5 hours. The mixture was then evaporated in vacuo to an oily gum which was dissolved in ethyl acetate (50 ml). The resultant organic solution was extracted with saturated aqueous sodium bicarbonate solution (50 ml) and the aqueous extract was washed with ethyl acetate. The aqueous extract was layered with ethyl acetate (30 ml) and was then acidified to pH 0.5 by addition of concentrated hydrochloric acid, and was then extracted with ethyl acetate (3×30 ml) and the combined organic extracts were dried (sodium sulphate) and evaporated in vacuo to a white foam. Trituration of this foam with di-isopropyl ether gave an off-white solid which was redissolved in ethyl acetate. Addition of di-isopropyl ether (400 ml) to the ethyl acetate solution caused precipitation of a solid which after filtration and drying afforded the *title compound* (8.27 g) as a white solid; m.p. ($M_{50}^2$) 72°, $[\alpha]_D^{23}+38°$ (c 0.96, pH 7 phosphate buffer).

(b) (R and S)-1-Acetoxyethyl (6R,7R)-3-dimethoxyphosphoryl-carbamoyloxymethyl-7-[Z-2-(fur-2-yl)-2-methoxyiminoacetamido]-ceph-3-em-4-carboxylate and (R and S)-1-acetoxyethyl (4R,6R,7R)-3-dimethoxyphosphorylcarbamoyloxymethyl-7-[Z-2-(fur-2-yl)-2-methoxyiminoacetamido]-ceph-2-em-4-carboxylate Potassium carbonate (0.55 g) was added to a stirred mixture of (6R,7R)-3-dimethoxyphosphorylcarbamoyloxymethyl-7-[Z-2-(fur-2-yl)-2-methoxyiminoacetamido]ceph-3-em-4-carboxylic acid (4.26 g) in dimethylformamide (10 ml) at room temperature. Stirring was continued for 1.5 hours by which time most of the potassium carbonate had dissolved.

The reaction mixture was then cooled to 0° and a solution of (R,S)-1-acetoxyethyl bromide (1.47 g) in DMF (5 ml) was added. The resultant solution was stirred at 0° for 1 hour and was then partitioned between 2 N-hydrochloric acid (100 ml) and ethyl acetate (100 ml). The aqueous phase was further extracted with ethyl acetate (2×50 ml) and the combined organic extracts were washed successively with 2 N-hydrochloric acid (2×100 ml), water (2×100 ml), saturated aqueous sodium bicarbonate solution (2×100 ml), water (2×100 ml), saturated brine (100 ml) and dried (sodium sulphate) and evaporated in vacuo to a foam. A solution of this foam in ethyl acetate (10 ml) was precipitated from diisopropyl ether to give a mixture of *the title esters* (2.01 g) as a white solid; $\nu_{max}$ (Nujol) 3180 to 3150 (2×NH), 1790 (β-lactam), 1764 ($CO_2R$), and 1680 and 1538 cm$^{-1}$ (CONH). The n.m.r. spectrum (DMSO-d$_6$) indicated at approximate Δ$^3$:Δ$^2$-isomer ratio of 3:2.

(c) (R and S)-1-Acetoxyethyl (1S,6R,7R)-3-Dimethoxyphosphorylcarbamoyloxymethyl-7-[Z-2-(fur-2-yl)-2-methoxyiminoacetamido]ceph-3-em-4-carboxylate, 1-oxide m-Chloroperbenzoic acid (0.944 g) in dichloromethane (10 ml) was added at 0° to a stirred solution of two batches of (R and S)-1-acetoxyethyl (6R,7R)-3-dimethoxyphosphorylcarbamoyloxymethyl-7-[Z-2-(fur-2-yl)-2-methoxyiminoacetamido]ceph-3-em-4-carboxylate and its Δ$^2$ isomer (ratio ca 3:2) (3.34 g) in dry dichloromethane (20 ml). After 25 minutes reaction was not complete (by t.l.c) so another portion of m-chloroperbenzoic acid (93 mg) was added and the reaction mixture was stirred for a further 10 minutes and evaporated in vacuo to a foam. T.l.c. indicated incomplete oxidation so the foam was re-dissolved in dichloromethane and treated with further m-chloroperbenzoic acid (0.236 g) for 20 minutes by which time reaction was complete. The reaction mixture was then evaporated in vacuo to a foam which was dissolved in ethyl acetate (5 ml) and precipitated from excess di-isopropyl ether to give the title compound (3.033 g) as a pale-yellow solid, m.p. (M$_{130}$$^2$) 150°, [α]$_D$$^{22}$+67.5° (c 0.98, DMSO).

(d) (R and S)-1-Acetoxyethyl (6R,7R)-3-Dimethoxyphosphorylcarbamoyloxymethyl-7-[Z-2-(fur-2-yl)-2-methoxyiminoacetamido]ceph-3-em-4-carboxylate Potassium iodide (2.50 g) and acetyl chloride (0.56 ml) were successively added, at 0°, to a solution of the product of (b) above (2.38 g) in dimethylformamide (15 ml).

The reaction mixture was stirred for 70 minutes at 0° and was then partitioned between ethyl acetate (100 ml) and 2 N-hydrochloric acid (100 ml). The aqueous phase was extracted with ethyl acetate (2×50 ml) and the combined organic extracts were successively washed with 2 N-hydrochloric acid (100 ml), aqueous sodium metabisulphite solution (2×100 ml), 2 N-hydrochloric acid (100 ml), water (100 ml), saturated aqueous sodium bicarbonate solution (100 ml), water (100 ml) and saturated brine (100 ml). The organic extract was dried (magnesium sulphate) and evaporated in vacuo to a yellow foam which on precipitation from diisopropyl ether afforded the title ester (1.722 g) as a pale-yellow solid, m.p. (M$_{70}$$^2$) 101°, [α]$_D$$^{22.5}$+22.4° (c 0.89, DMSO).

(e) (R and S)-1-Acetoxyethyl (6R,7R) 3-phosphonocarbamoyloxymethyl-7-[Z-2-(fur-2-yl)-2-methoxyiminoacetamido]ceph-3-em-4-carboxylate Bromotrimethylsilane (0.31 g) in dichloromethane (3 ml) was added to a cooled (0°) stirred mixture of (R and S)-1-acetoxyethyl (6R,7R)-3-dimethoxyphosphorylcarbamoyloxymethyl-7-[Z-2-(fur-2-yl)-2-methoxyiminoacetamido]ceph-3-em-4-carboxylate (0.62 g) and trimethylsilylurethane (0.16 g) in dry dichloromethane (12 ml) in a nitrogen atmosphere. After 2.5 hours the reaction mixture was evaporated in vacuo to a foam. This foam was dissolved in ethyl acetate (30 ml) although a slight precipitate remained. The filtered organic solution was treated with saturated aqueous sodium bicarbonate solution (30 ml) and the aqueous solution was layered with butan-1-ol (20 ml) and acidified to pH 0.5 by addition of concentrated hydrochloric acid. The aqueous phase was extracted with butan-1-ol (2×15 ml) and the combined organic extracts were evaporated in vacuo to give a solid. Trituration of this solid with di-isopropyl ether afforded the title ester (0.396 g) as a solid; ν$_{max}$ (Nujol) 3270 (NH), 1788 (β-lactam), 1734 (CO$_2$R) and 1684 and 1540 cm$^{-1}$ (CONH); τ (DMSO-d$^6$)0.18 (d, J 8 Hz, NH), 2.9 to 3.4 (broad m, 2 superimposed q, CHCH$_3$), 4.14 (m, 7-H), mixture of diastereoisomers), 4.76 (m, 6-H, mixture of diastereoisomers), 7.92 (s, OCOCH$_3$) and 8.52 (d, J 5 Hz, CHCH$_3$).

EXAMPLE 1

(6R,7R)-3-Carbamoyloxymethyl-7-aZ-2-(fur-2-yl)-2-methoxyiminoacetamido]ceph-3-em-4-carboxylic acid (cefuroxime)

A solution of (6R,7R)-3-phosphonocarbamoyloxymethyl-7-[Z-2-(fur-2-yl)-2-methoxyiminoacetamido]ceph-3-em-4-carboxylic acid (0.35 g) in water (4 ml) and dioxan (1 ml) was kept successively at 40° for 5 hours, room temperature for 16 hours, 40° for 6 hours and 20° for 16 hours. The conversion to the *title compound* was monitored by t.l.c. A precipitate was formed and this was filtered off. The pH was altered from 4 to 7 by addition of saturated aqueous sodium bicarbonate solution.

The resultant mixture was washed with ethyl acetate (25 ml) and the aqueous phase was acidified to pH2 (with concentrated hydrochloric acid) which was extracted with ethyl acetate (3×25 ml). The organic extracts were combined and washed successively with water and saturated brine, dried (magnesium sulphate) and evaporated in vacuo to an oil. Trituration of this oil with ether afforded the *title compound* as a solid (41 mg) with ultraviolet (pH6 phosphate buffer) and n.m.r. (DMSO-d$^6$) spectra in accord with an authentic specimen.

EXAMPLE 2

Cefuroxime

A solution of (6R,7R)-3-phosphonocarbamoyloxymethyl-7-[Z-2-(fur-2-yl)-2-methoxyiminoacetamido]ceph-3-em-4-carboxylic acid, trisodium salt, trihydrate (1.25 g) in water (40 ml) had its pH adjusted from 6.9 to 3.5 by addition of 2 N-hydrochloric acid and saturated aqueous NaHCO$_3$ and was kept at 40° for 3.75 hours.

The pH of the reaction mixture was kept at ca. 3.5 by periodic addition of portions of 2 N-hydrochloric acid. After 3.75 hours, saturated aqueous sodium bicarbonate was added to give a pH of 7 and the solution was washed with ethyl acetate (50 ml) and then covered with further ethyl acetate (50 ml). The organic phase was acidified to pH 2 with orthophosporic acid, and then extracted with ethyl acetate (50 ml). The combined organic phases were washed with water (2×50 ml) and saturated brine (50 ml), then dried over magnesium sulphate and evaporated in vacuo to give the *title compound* (0.600 g) as a white solid [α]$_D$$^{21}$+51° (c 1.00, DMSO), λ$_{max}$ (pH 6 phosphate buffer) 275 nm (E$_1$ $_{cm}$$^{1\%}$ 422, ε 17 900).

EXAMPLE 3

(R and S)-1-Acetoxyethyl (6R,7R)-3-carbamoyloxymethyl-7-[Z-2-(fur-2-yl)-2-methoxyiminoacetamido]ceph-3-em-4-carboxylate A solution of (R and S)-1-acetoxyethyl (6R,7R)-3-phosphonocarbamoyloxymethyl-7-[Z-2-(fur-2-yl)-2-methoxyiminoacetamido]ceph-3-em-4-carboxylate (0.226 g) in tetrahydrofuran (5 ml) and pH 4 buffer (20 ml) was kept at pH 4 for 3.75 hours at 40°.

The solution was poured into saturated aqueous sodium bicarbonate (20 ml) and extracted with ethyl acetate (2×20 ml). The organic phase was washed with water (2×20 ml) and saturated brine (20 ml) then dried over magnesium sulphate and evaporated to an oil (0.092 g) which, after precipitation from ethyl acetate-petrol (b.p. 40° to 60°) gave the *title ester* (0.054 g) as a solid; $[\alpha]_D^{22} +57.3°$ (c 1.08, DMSO), $\lambda_{max}$ (CHCl$_3$) 281 nm (E$_{1\ cm}^{1\%}$ 289, $\epsilon$ 14 750).

We claim:

1. In a process for the preparation of a 3-carbamoyloxymethyl cephalosporin of formula

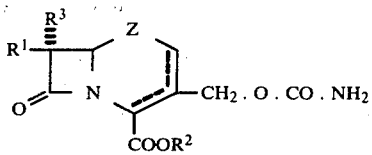

(II)

wherein R$^1$ represents a C$_1$–C$_{40}$ protected amino group; R$^2$ represents a group selected from the group consisting of hydrogen atoms and carboxy blocking groups; R$^3$ represents a group selected from the group consisting of hydrogen atoms and C$_1$–C$_8$ alkyl, C$_1$–C$_8$ alkylthio and C$_1$–C$_8$ alkoxy groups; Z is >S or >S→O ($\alpha$- or $\beta$-); and the dotted line bridging the 2-, 3- and 4-positions of the molecule indicates that the compounds may be ceph-2-em or ceph-3-em compounds and salts thereof, the step which consists in hydrolysing a compound of formula

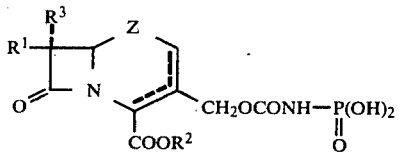

wherein R$^1$, R$^2$, R$^3$, Z and the dotted line are as hereinbefore defined, and salts thereof.

2. The process of claim 1 wherein the hydrolysis is effected at a pH below 5.

3. In a process for the preparation of (6R,7R)-3-carbamoyloxymethyl-7-[Z-2-(fur-2-yl)-2-methoxyiminoacetamido]-ceph-3-em-4-carboxylic acid, the step which consists of hydrolysing (6R,7R)-3-phosphonocarbamoyloxymethyl-7-[Z-2-(fur-2-yl)-2-methoxyiminoacetamido]ceph-3-em-4-carboxylic acid at a pH in the range of 3 to 4.

* * * * *